United States Patent [19]
Yasuda

[11] Patent Number: 4,676,638
[45] Date of Patent: Jun. 30, 1987

[54] LIGHT-TRANSMISSIBLE FOREIGN OBJECT SENSOR

[75] Inventor: Shigekazu Yasuda, Aichi, Japan

[73] Assignee: Kabushiki Kaisha Tokai Rika Denki Seisakusho, Aichi, Japan

[21] Appl. No.: 595,337

[22] Filed: Mar. 30, 1984

[30] Foreign Application Priority Data

Mar. 31, 1983 [JP] Japan .............................. 58-47431[U]
Mar. 31, 1983 [JP] Japan .............................. 58-47432[U]

[51] Int. Cl.$^4$ ........................................... G01N 21/41
[52] U.S. Cl. .................................... 356/237; 250/573; 318/483; 318/DIG. 2; 356/136
[58] Field of Search .................... 356/37, 38, 136, 239, 356/240; 250/564, 573, 574; 73/29; 318/444, 483, DIG. 2

[56] References Cited

U.S. PATENT DOCUMENTS 4,481,450 11/1984 Watanabe et al. ................... 318/444

FOREIGN PATENT DOCUMENTS 2420594 11/1975 Fed. Rep. of Germany .

Primary Examiner—Davis L. Willis
Assistant Examiner—Matthew W. Koren
Attorney, Agent, or Firm—Finnegan, Henderson Farabow Garrett and Dunner

[57] ABSTRACT

A sensor for detecting a light-transmissible foreign object, such as a raindrop, attached on a transparent body, such as a windowglass of a vehicle includes a light source, a light receiving unit disposed on the inside of the transparent body, and a prism fixedly attached on the transparent body on the inside thereof and arranged in a manner so that the light emitted toward the transparent body from the light source is caused to advance through the prism to reach the light receiving unit and that the quantity of light received by the light receiving unit changes when a light-transmissible foreign object attaches on the outside of the transparent body. The prism includes a restriction surface for preventing external light which enters the prism through the transparent body from coming into the light receiving unit.

7 Claims, 9 Drawing Figures

LIGHT-TRANSMISSIBLE FOREIGN OBJECT SENSOR

FIELD OF THE INVENTION

The present invention relates to a light-transmissible foreign object sensor, more particularly to a raindrop sensor, for detecting a raindrop on a windshield or windowglass of a vehicle.

BACKGROUND OF THE INVENTION

There has been proposed a foreign object sensor, for example a raindrop sensor, wherein a prism, a light emitting unit (light source), and a light receiving unit are disposed, inside of a windshield or windowglass of a vehicle. The light impinging on the windowglass from the light emitting unit through the prism is totally reflected at a boundary surface between the windowglass and the outside air and the reflected light is received by the light receiving unit. If there is a raindrop on the outer surface of the windowglass, a part of the light impinging on the windowglass escapes though the raindrop so that the quantity of reflected light, that is the quantity of light received by the light receiving unit, decreases. This causes a change in the output of the light receiving unit indicating the presence of a raindrop.

There is a problem in the raindrop sensor described above because not only is it required to provide a complex processing circuit for eliminating disturbance by external light, for example sunlight, impinging on the light receiving unit through the prism from the outside of the windowglass, but it also may become impossible to perform raindrop detection because the light receiving unit is saturated by the external light.

OBJECTS AND SUMMARY OF THE INVENTION

It is an object of the present invention to detect the presence of a light-transmissible foreign object on one side of a transparent body by means of variations in light received by a light sensor.

Another object of the present invention is a sensor for detecting the presence of a light-transmissible foreign object on one side of a transparent body which is not affected by ambient light transmitted through the transparent body.

Yet another object of the present invention is a compact, simple, and inexpensive sensor for detecting the presence of a light-transmissible foreign object on the side of a transparent body.

Still another object of the present invention is a sensor which uses the principles of optical reflection and refraction for detecting the presence of a light-transmissible foreign object on one side of a transparent body.

These and other objects are accomplished by a sensor for detecting the presence of a light-transmissible foreign object on one side of a transparent body comprising a light source on another side of the transparent body, the another side being opposite the one side of the transparent body, light receiving means on the another side of the transparent body, and prism means in contact with the another side of the transparent body for the transmission of light from the light source and the light receiving means such that the presence of a light-transmissible foreign object on the one side of the transparent body in the area of contact of the prism means with the another side of the transparent body causes a detectable variation in the level of light received by the light receiving means to indicate the presence of the light-transmissible foreign object on the transparent body.

BRIEF DESCRIPTION OF THE DRAWINGS

These and other objects, features, and advantages of the present invention, as well as the invention itself, will become more apparent to those skilled in the art when considered in the light of the accompanying drawings, wherein.

DETAILED DESCRIPTION OF THE PREFERRED EMBODIMENTS

Figure 1:
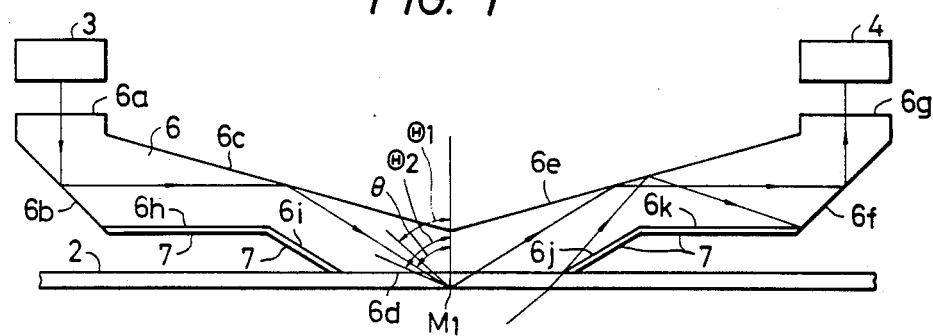
FIG. 1 is a side view of an embodiment of the sensor according to the present invention.

FIG. 1 shows a preferred embodiment of the present invention. In FIG. 1, a light emitting unit (light source) 3, a light receiving unit 4, and a prism 6 having surfaces $6a \sim 6k$ are provided inside a windowglass 2.

In this embodiment, each of the surface $6b$, $6c$, $6e$ and $6f$ of the prism 6 is inclined by a predetermined angle so that light impinging thereon is totally reflected. That is, each of the reflex surfaces $6b$ and $6f$ is inclined by 45° with respect to a surface $6d$ bonded on the inner surface of the windowglass 2. Each of the reflex surfaces $6c$ and $6e$ is inclined by 15° with respect to the surface $6d$. The surface $6d$ is bonded on the windowglass 2 in a manner so that no reflection occurs in the boundary surface of the windowglass 2.

A light absorbing layer 7 is formed by applying black paint or the like on each of surfaces $6h$, $6i$, $6j$ and $6k$ of the prism 6. The surfaces $6h$ and $6k$ are arranged to be substantially parallel with the surface $6d$.

The light coming into the prism 6 through the surface $6a$ from the light emitting unit 3 is reflected twice at the reflex surfaces $6b$ and $6c$, respectively, and then is transmitted into the windowglass 2. The angle of incidence, $\theta$, to the windowglass is set as follows:

$$\theta_1 < \theta < \theta_2$$

where $\theta_1$ represents the critical angle at the boundary surface $M_1$ of the windowglass 2 with respect to the external air, and $\theta_2$ represents the critical angle at the boundary surface $M_2$ (FIG. 2) of the windowglass 2 with respect to a raindrop 5 attached on the outer surface of the windowglass 2.

Assuming the refractive indices of the windowglass 2 and air are 1.5 and 1.0, respectively, the critical angle $\theta_1$ is 45° or less. Assuming the refractive index of the raindrop 5 is 1.33, the critical angle $\theta_2$ is 62° or more.

In this embodiment, the tilt angles of the reflex surfaces 6b and 6c are 45° and 15° respectively, and, therefore, the angle of incidence $\theta$ is 60°.

Accordingly, when no raindrop 5 attaches on the windowglass 2, the light coming into the windowglass 2 from the light source 3 is perfectly reflected at the boundary surface $M_1$, back into the prism 6, and is further reflected repeatedly on the reflex surfaces 6e and 6f, to enter the light receiving unit 4 through the surface 6g.

Figure 2:
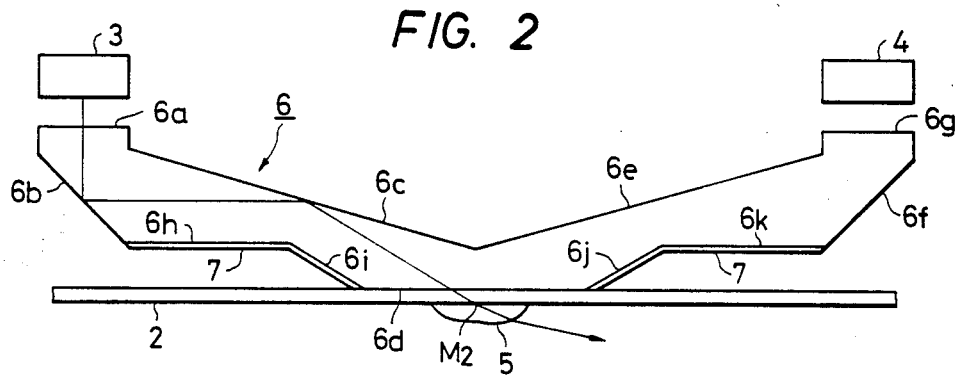
FIG. 2 is the same side view as FIG. 1 but shows an attached light-transmissible object.

If a raindrop 5 is present on the windowglass 2, as shown in FIG. 2, the light coming into the windowglass 2 is transmitted into the raindrop 5 through the boundary surface $M_2$. The majority of the light entering the raindrop 5 is transmitted through the raindrop 5 to the outside. A portion of the light, however, is reflected inward at the boundary surface between the raindrop and the external air. As a result, the quantity of reflected light received by the light receiving unit 4 is decreased.

Although external light may enter the prism 6 through the surface 6d from the outside of the windowglass 2, this external light cannot be reflected so as to reach the light receiving unit 4.

Figure 3:
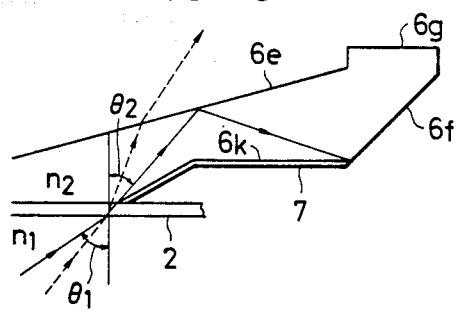
FIG. 3 is a diagram explaining the function of the sensor of FIG. 1.

Referring to FIG. 3, the reason why the external light cannot reach the light receiving unit 4 will be described. In accordance with the law of refraction, the following relation holds:

$$n_1 \sin \theta_1 = n_2 \sin \theta_2$$

where $n_1$ represents the refractive index of air, $n_2$ the refractive index of the combination of the windowglass 2 and the prism 6, $\theta_1$ the angle of incidence of the external light to the windowglass 2, and $\theta_2$ the refractive angle when the external light passes through the windowglass 2 and the prism 6.

Now, let the refractive index $n_1$ be replaced by 1 and $\theta_1$ by 90°. The critical angle in the prism 6 is obtained as follows:

$$\sin 90° = n_2 \sin \theta_2$$

$$\therefore \sin \theta_2 = 1/n_2$$

$$\therefore \text{critical angle} = \sin^{-1} 1/n_2$$

That is, the refractive angle $\theta_2$ of the external light is as follows even if the external light enters at any angle of incidence:

$$\theta_2 < \sin^{-1} 1/n_2$$

Accordingly, the external light comes out of the prism 6 through the surface 6c or 6e or advances toward a surface 6h or 6k after it has been totally reflected at the surface 6c or 6e. If the surfaces 6h and 6k are arranged to have a sufficient length, the external light will be absorbed in the light absorbing layer 7 even though the external light has been totally reflected at the surface 6e. In this manner, the external light is prevented from being reflected by the surface 6f into the light receiving unit 4.

Although not shown in the drawing, the output of the light receiving unit 4 may be connected to a drive unit of a window wiper mechansims provided on a vehicle so that the drive unit begins to drive the wiper when the output of the light receiving unit 4 decreases by a predetermined value as a result of rain.

The operation of the above-mentioned first embodiment will now be described.

When no raindrop 5 is present on the outside of the windowglass 2, the light from the light emitting unit 3 enters the windowglass 2 after it has been repeatedly totally reflected by the surfaces 6b and 6c. It is then totally reflected at the boundary surface $M_1$. The reflected light comes into the prism 6 again, and it is repeatedly reflected on the reflex surfaces 6e and 6f. Thereafter, the reflected light comes out of the surface 6g and enters the light receiving unit 4.

If a raindrop 5 is present, on the other hand, the light from the light emitting unit 3 enters the raindrop 5 through the windowglass 2 and a part of the light escapes outside out of the raindrop 5 so that the quantity of light received by the light receiving unit 4 decreases. In this manner, the presence of the raindrop is detected by a change in the output of the light receiving unit 4. A wiper unit provided on a vehicle may be started as a result.

At this time, the external light entering the prism 6 through the surface 6d from the windowglass 2 comes out of the prism 6 through the surface 6e, or it is absorbed by the light absorbing layer 7 on the surface 6k after it has been reflected at the surface 6e. The light receiving unit 4 is prevented from being saturated by the external light.

Figure 4:
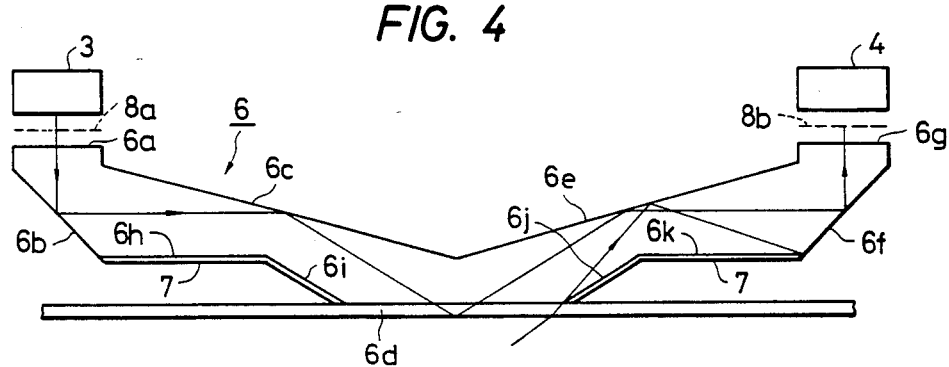
FIG. 4 is a side view of another embodiment of the sensor according to the present invention.
Figure 5:
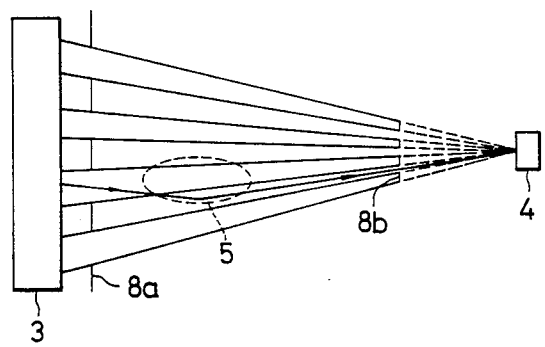
FIG. 5 is a diagram explaining the function of the sensor of FIG. 4.

FIGS. 4 and 5 show a second embodiment of the present invention. The same reference numerals are used in the first embodiment for the same part or component to limit the description to new elements. Further, this second embodiment is arranged in the same manner as the first embodiment except that a pair of slits 8a and 8b are additionally provided between the light emitting unit 3 and the surface 6a and between the light receiving unit 4 and the surface 6g, respectively. The slit 8b is provided for preventing the light which advances in the prism 6 after it has passed through the slit 8a from passing therethrough, so that the light from the light emitting unit 3 cannot enter the light receiving unit 4.

When a raindrop 5 is present, a part of the light entering the raindrop 5 is refracted when it is reflected at the boundary surface between the raindrop 5 and the air outside the raindrop 5 and, therefore, it can pass through the slit 8b. In the second embodiment, when no raindrop 5 is present, the light does not enter the light receiving unit 4 so that the output of the light receiving unit 4 is, for example, at a low level. If a raindrop 5 is present, however, the light is refracted by the raindrop 5 so that a part thereof is allowed to enter the light receiving unit 4. The output of the light receiving unit 4 is changed to a higher level to detect the presence of the raindrop 5.

In this second embodiment, the detection of the raindrop 5 will not be affected by a change in the quantity of light emitted from the light emitting unit 3 due to the deterioration of the light emitting unit 3 or due to electrical noise.

Figure 6:
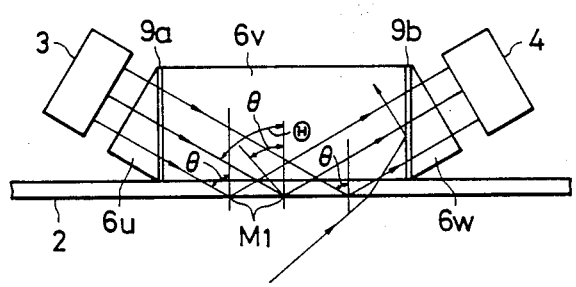
FIG. 6 is a side view of another embodiment of the sensor according to the present invention.
Figure 7:
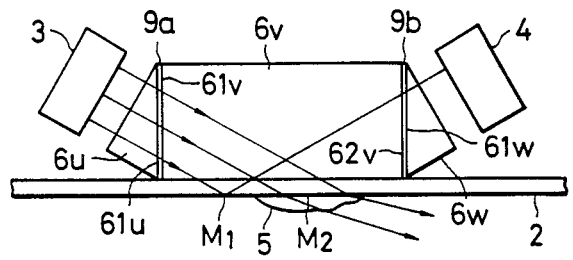
FIG. 7 is the same side view as FIG. 6 but shows an attached light-transmissible object.

FIGS. 6 and 7 show a third embodiment in which the same reference numerals as used in the first embodiment designate the same parts or components.

In this third embodiment, a prism 6 is constituted by three prism pieces 6u, 6v, and 6w. The prism piece 6v is bonded such that no reflection is generated at the boundary surface between the prism piece 6v and the windowglass 2. Each of the prism piece 6u and 6w is a triangular prism, while the prism piece 6v is a rectangular prism. The prism piece 6v is disposed between the prism pieces 6u and 6w.

The angle of incidence $\theta$ of the light coming into the windowglass 2 through the prism pieces 6u and 6v from the light emitting unit 3 is set, similarly to the case of the first embodiment:

$$\theta_1 < \theta < \theta_2$$

where $\theta_1$ represents the critical angle at the boundary surface $M_1$ between the windowglass 2 and the external air, and $\theta_2$ represents the critical angle at the boundary surface $M_2$ between the windowglass 2 and a raindrop 5 present on the outer surface of the windowglass 2 (FIG. 7).

Accordingly, when no raindrop 5 is present on the outside of the windowglass 2, the light entering the windowglass 2 from the light emitting unit 3 is totally reflected at the boundary surface $M_1$, comes into the prism piece 6v again, and reaches the light receiving unit 4 through the prism piece 6w.

If a raindrop 5 is present, a part of the light entering the windowglass 2 passes into the raindrop 5 through the boundary surface $M_2$. The main part of the light entering the raindrop 5 passes out of the raindrop 5 and a smaller part is reflected inwardly at the boundary surface between the raindrop and the external air. The quantity of reflected light, received by the light receiving unit 4 decreases.

Small air gaps 9a and 9b are formed between a surface 61u of the prism piece 6u and a surface 61v of the prism piece 6v and between a surface 62v of the prism piece 6v and a surface 61w of the prism piece 6w, respectively. Each of the surfaces 61u and 62v is arranged to be substantially perpendicular to the inner surface of the windowglass 2 to reflect totally the external light coming into the prism piece 6v from the windowglass 2.

Figure 8:
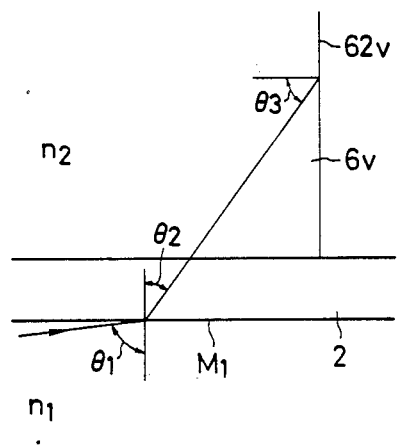
FIG. 8 is a diagram for explaining the function of the sensor of FIG. 7.

Referring to FIG. 8, the reason why the external light is totally reflected at the surfaces 61u and 62v will be described. In accordance with the law of refraction, the following relation holds:

$$n_1 \sin \theta_1 = n_2 \sin \theta_2$$

where $n_1$, $n_2$, $\theta_1$ and $\theta_2$ are the same as those described with respect to the first embodiment by referring to FIG. 3. Accordingly, in the same manner as the case of the first embodiment, the critical angle in the prism 6 is obtained as follows:

Let the refractive index $n_1$ be replaced by 1 and $\theta_1$ by 90°, and $$\sin 90° = n_2 \sin \theta_2$$

$$\therefore \sin \theta_2 = 1/n_2$$

$$\therefore \text{critical angle} = \sin^{-1} 1/n_2$$

That is, the refractive angle $\theta_2$ of the external light is as follows even if the external light enters at any angle of incidence:

$$\theta_2 < \sin^{-1} 1/n_2$$

In order to reflect the light entering the prism piece 6v at the surface 62v totally, the following relation holds:

$$\sin^{-1} 1/n_2 < \theta_3$$

$$\therefore \theta_2 < \sin^{-1} 1/n_2 < \theta_3 \quad (1)$$

Since the 62v is substantially perpendicular to the boundary surface $M_1$, $$\theta_2 + \theta_3 = 90° \quad (2)$$

From the equation (1), $$\theta_2 < \theta_3 \quad (3)$$

From the equation (2), $$\theta_3 = 90° - \theta_2 \quad (4)$$

Substituting the equation (4) into the equation (3), $$\theta_2 < 90° - \theta_2$$

$$\therefore \theta_2 < 45°$$

Similarly, the following relation is obtained:

$$\theta_2 < 45° < \theta_3$$

Accordingly, if the critical angle is smaller than 45°, the angle $\theta_2$ is smaller than 45°, and the angle $\theta_3$ becomes larger than 45°, that is, than the critical angle, so that the light is totally reflected at the surface 62v.

From the condition that the critical angle = $\sin^{-1} 1/n_2 < 45°$, $n_2 > 1.414$ is obtained, and all the external light can be totally reflected at the surface 62v if the refractive index of the prism 6 is selected to be larger than 1.414.

Although not shown in the drawing, the output of the light receiving unit 4 may be connected to a drive unit of a wiper mechanism provided on a vehicle so that the drive unit begins to drive the wiper when the output of the light receiving unit 4 decreases to a predetermined value.

The operation of the above-mentioned third embodiment will now be described.

When no raindrop 5 is present on the outside of the windowglass 2, the light from the light emitting unit 3 enters the windowglass 2 through the prism piece 6u, the air gap 9a, and the prism piece 6v, and reenters the prism piece 6v after being perfectly reflected from the boundary surface $M_1$. The light then enters the light receiving unit 4 through the air gap 9b and the prism piece 6w.

If a raindrop 5 is present, a part of the light from the light emitting unit 3 escapes out of the raindrop 5 so that the quantity of light received by the light receiving unit 4 decreases. In this manner, the presence of a raindrop is detected by the change of output of the light receiving unit 4. A wiper unit provided on a vehicle may be started as a result.

The external light entering the prism piece 6v from the windowglass 2 is perfectly reflected at the surface 62v and is prevented from entering the light receiving unit 4 so that there is no risk of saturation of the light receiving unit 4 due to the external light.

Figure 9:
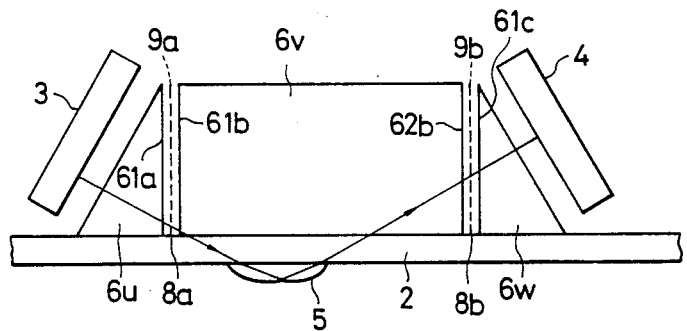
FIG. 9 is a side view of yet another embodiment of the sensor according to the present invention.

FIG. 9 shows a fourth embodiment of the present invention. In this fourth embodiment, slits 8a and 8b, which are similar to those employed in the second embodiment, are inserted in the air gaps 9a and 9b of the prism 6 of the third embodiment.

The function of these slits 8a and 8b is quite the same as in the second embodiment. That is, when no raindrop 5 is present, the light from the light emitting unit 3 enters through the prism piece 6u, the slits 8a, and the prism piece 6v, and reaches the slit 8b through the prism piece 6v after being totally reflected at the boundary surface $M_1$ (FIG. 6). The slit 8b prevents the light from entering the light receiving unit 4 so that the output of the light receiving unit 4 is, for example, at a low level. If a raindrop 5 is present, the light entering the raindrop is refracted when it is reflected at the boundary surface between the raindrop 5 and the outside air so that a part thereof is allowed to enter the light receiving unit 4 through the slit 8b. As a result, the output of the light receiving unit 4 is changed to a high level to enable detection of the raindrop 5.

In this fourth embodiment, as described with respect to the second embodiment, the detection of the raindrop 5 cannot be affected by a change in the quantity of light emitted from the light emitting unit 3 due to the deterioration of the light emitting unit 3 or to electrical noises.

Although the light emitting unit 3 is illustrated such that it is disposed inside the windowglass 2 in all the embodiments described above, the same function and effect can be obtained even if it is disposed outside the windowglass 2.

Although the present invention is illustrated as a means to detect a raindrop 5, the present invention may be applied to a sensor for detecting any similar droplets as well as a sensor for detecting a blur on glass.

While the salient features of the invention have been described with reference to the drawings, it should be understood that the preferred and alternate embodiments described herein are susceptible of modification and alteration without departing from the spirit and scope of the following claims.

What is claimed is:

1. A sensor for detecting the presence of a light-transmissible foreign object on one side of a transparent body, the sensor comprising:
    a light source on another side of the transparent body, said another side being opposite the one side of the transparent body;
    light receiving means on said another side of the transparent body; and
    a prism for the transmission of light between said light source and said light receiving means, said prism comprising a plurality of prism pieces with at least one air gap between respective surfaces of two adjacent prism pieces, light from said light source passing through said gap and said surfaces, at least one of said respective surfaces comprising a restrictive surface for preventing ambient light transmitted through the transparent body into said prism pieces from reaching said light receiving means and said prism being in contact at an area having a non reflecting boundary with said another side of the transparent body, with the presence of a light-transmissible foreign object on the one side of the transparent body in the area of contact of said prism with said another side of the transparent body causing a detectable variation in the light received by said light receiving means to indicate the presence of the light-transmissible object on the transparent body.

2. A sensor for detecting the presence of a light-transmissible foreign object on one side of a transparent body, the sensor comprising:
    a light source on another side of the transparent body, said another side being opposite the one side of the transparent body;
    light receiving means on said another side of the transparent body; and
    a prism for the transmission of light between said light source and said light receiving means, said prism being in contact at an area having a non-reflecting boundary with said another side of the transparent body and said prism including multiple reflex surfaces for reflecting substantially all of the light from said light source through said prism to said light receiving means in the absence of a light-transmissible object on the one side of the transparent body and in the presence of a light-transmissible object on the one side of the transparent body in the area of contact of said transmission means with said another side of the transparent body causing a detectable variation in the light received by said light receiving means to indicate the presence of the light-transmissible object on the transparent body.

3. A sensor according to claim 2 wherein said prism further includes at least one light absorbing surface and wherein ambient light transmitted through the transparent body and into said prism is reflected internally in said prism to said light absorbing surface.

4. A sensor according to claim 3 further including:
    a first slit means disposed between said light source and said prism to permit only some of said light emitted from said light source to enter said prism; and
    second slit means disposed between said light receiving means and said prism to block said light entering said prism through said first slit means from being received by said light receiving means in the absence of a light-transmissible object on the one side of the transparent body opposite said non-reflecting bond and to permit said light entering said prism through said first slit means to be received by said light receiving means if a light-transmissible object is present on the one side of the transparent body opposite said non-reflecting bond.

5. A sensor for detecting the presence of a light-transmissible foreign object on one side of a transparent body, the sensor comprising:
    a light source on another side of the transparent body, said another side being opposite the one side of the transparent body;
    light receiving means on said another side of the transparent body;
    a prism for the transmission of light between said light source and said light receiving means, said prism comprising
    a central prism piece having first, second, and third planar surfaces, said third planar surface being in contact at an area with said another side of the transparent body and bonded by a non-reflecting bond to said another side of the transparent body;
    an input prism piece between said light source and said central prism piece and having a planar surface substantially coextensive with said first planar surface of said central prism piece and being separated therefrom by a first air gap; and an output prism between said light receiving means and said central prism piece and having a planar surface substantially coextensive with said second planar surface of said central prism piece and being separated therefrom by a second air gap, said second air gap, said second planar surface, and said planar surface of said output prism piece preventing ambient light transmitted through the transparent body into said central prism piece from being reflected within said central prism piece and said output prism piece to said light receiving means, with the presence of a light-transmissible foreign object on the one side of the transparent body in the area of contact of said prism with said another side of the transparent body causing a detectable variation in the light received by said light receiving means to indicate the presence of the light-transmissible object on the transparent body.

6. A sensor according to claim 5 wherein said input and output prism pieces are triangular in cross-section and said central prism piece is rectangular in cross section.

7. A sensor according to claim 5 further including:

a first slit means disposed in said first air gap to permit only some of said light transmitted through said first prism piece from said light source to enter said central prism piece; and a second slit means disposed in said second air gap to block any light passing through said first slit means from being received by said light receiving means in the absence of a light-transmissible object on the one side of the transparent body opposite said non-reflecting bond and to permit said light passing through said first slit means to be received by said light receiving means if a light-transmissible object is present on the one side of the transparent body opposite said non-reflecting bond.

* * * * *